United States Patent
Ramamurthy et al.

(10) Patent No.: US 6,436,047 B1
(45) Date of Patent: Aug. 20, 2002

(54) APERTURE CONFIGURATIONS FOR MEDICAL DIAGNOSTIC ULTRASOUND

(75) Inventors: Bhaskar S. Ramamurthy, San Jose; Stuart L. Carp, Menlo Park; Albert Gee, Los Altos, all of CA (US)

(73) Assignee: Acuson Corp., Mountain View, CA (US)

( * ) Notice: Subject to any disclaimer, the term of this patent is extended or adjusted under 35 U.S.C. 154(b) by 0 days.

(21) Appl. No.: 09/723,048

(22) Filed: Nov. 27, 2000

Related U.S. Application Data (63) Continuation-in-part of application No. 09/200,663, filed on Nov. 25, 1998, now Pat. No. 6,174,286.

(51) Int. Cl.⁷ .................................................. A61B 8/00
(52) U.S. Cl. ........................................................ 600/447
(58) Field of Search .................................. 600/437, 443, 600/447; 73/625–626

(56) References Cited

U.S. PATENT DOCUMENTS

| | | | | |
|---|---|---|---|---|
| 4,168,628 A | * | 9/1979 | Vilkomerson | 73/626 |
| 4,398,539 A | * | 8/1983 | Proudian | 73/626 |
| 4,665,924 A | * | 5/1987 | Saito et al. | 73/631 |
| 5,617,862 A | * | 4/1997 | Cole et al. | 600/447 |

* cited by examiner

Primary Examiner—Francis J. Jaworski (57) ABSTRACT

A method and system for obtaining ultrasound data is provided. Different aperture techniques are used for transmit than on receive. The various techniques include synthetic aperture, shorting elements, skipping elements, sliding apertures and combinations thereof. The techniques used may also vary as a function of the depth of field.

34 Claims, 11 Drawing Sheets

ELEMENT SKIPPING ON TRANSMIT

EVEN ELEMENTS FOR TRANSMIT AND RECEIVE OF ACQUISITION2

ODD ELEMENTS FOR TRANSMIT AND RECEIVE OF ACQUISITION 1

APERTURE CONFIGURATIONS FOR MEDICAL DIAGNOSTIC ULTRASOUND

CROSS REFERENCE TO RELATED APPLICATION

This application is a continuation-in-part of co-pending U.S. patent application No. Ser. 09/200,663, filed Nov. 25, 1998 and now U.S. Pat. No. 6,174,286, which is hereby incorporated by reference in its entirety.

BACKGROUND

This invention relates to an ultrasound system and method for obtaining ultrasound data using transducer element switching. In particular, switching is used to space apart or short elements together for at least one transmission or reception of acoustic energy, and the resulting reflected echo signals are processed to obtain ultrasound data.

Ultrasound systems generally include transmitters (transmit channels), receivers, processors to control image formation and display monitors. Power supplies drive the transmitters, and control circuitry controls the ultrasound system. The transmitter provides electrical excitation waveforms to a transducer. The electric excitation waveforms are converted to acoustic energy by the transducer for imaging a target. The transducer generally includes a plurality of transducer elements which may be individually excited by respective plurality of transmitters, so each transmitter is connected to one element at any given time.

In a system providing a variable aperture, each one of a plurality of transmit channels may be connected to any one of several transducer elements using a multiplexer. One example of such a variable aperture multiplexer structure is disclosed by Cole et al. in U.S. Pat. No. 5,617,862.

The variable aperture multiplexer structure may be modified to allow a transmit channel to connect to more than one element at a time. As disclosed by Cole et al., switching means and programmability to support adjacent element shorting is provided. In order to connect one transmitter to two or more transducer elements, a multiplexer module in addition to a standard configuration is provided. In one example, the adjacent element shorting structure is used for a transducer with λ/4-spacing of transducer elements. Cole et al. further describes connecting inner and outer elements for simultaneous transmit and receive (a type of multiplexer shorting). With reference to inner and outer active elements, filters for use in second harmonic imaging are disclosed at column 14, lines 5 through 25.

BRIEF SUMMARY

The present invention is defined by the following claims, and nothing in this section should be taken as a limitation on those claims. By way of introduction, the preferred embodiments described below include a method and system for obtaining ultrasound data. Different aperture techniques are used for transmit than on receive. The various techniques include synthetic aperture, shorting elements, skipping elements, sliding apertures and combinations thereof.

The techniques used may also or independently vary as a function of the position of the transmit focus. Any desired aperture is used for a first focal position. One or more of shorting elements, skipping elements, synthetic aperture and combinations thereof techniques are used for a second focal position deeper than the first focal position.

Further aspects and advantages of the invention are discussed below in conjunction with the preferred embodiments.

DETAILED DESCRIPTION OF THE INVENTION

In one preferred embodiment described below, at least one transmit or receive channel is connected to more than one transducer element for a transmit or receive event. For example, adjacent transducer elements are shorted together by a multiplexer. By shorting together transducer elements, a wider aperture using fewer channels may be obtained, tending to decrease the cost of a transmitter or receiver sub-system of the ultrasound system. Shorting adjacent transducer elements together may result in the generation of grating lobes along the azimuthal dimension. The effect of the grating lobes may be minimized by receiving ultrasound data and then obtaining ultrasound information associated with a harmonic of a fundamental transmit frequency.

Figure 1:
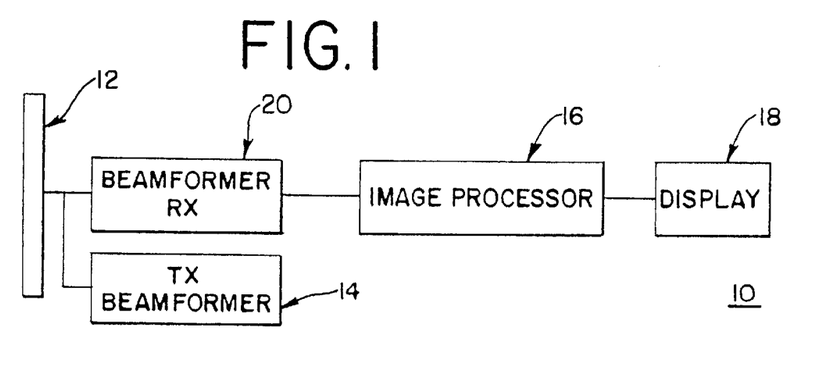
FIG. 1 is a block diagram of an ultrasound system for obtaining ultrasonic data and generating an ultrasound image.

Referring to FIG. 1, an ultrasound system for obtaining ultrasonic data and generating an image is shown at 10. The ultrasound system 10 includes a transducer 12, a transmit beamformer 14, a receive beamformer 20, an image processor 16, and a display 18. Other systems, such as systems with additional or different components, may be used. The various elements of FIG. 1 may be formed in any suitable manner, including a wide variety of conventional systems altered to operate as described below. The widest variety of beamformers, transducers, image processors and displays may be adapted for use with this invention. Both analog and digital beamformer systems are suitable. By way of example, without intending any limitation, the ultrasound imaging systems marketed by Acuson Corporation under the trade name Sequoia®, Aspen™ and 128XP® are capable of being modified to implement this invention. The Sequoia ultrasound imaging system is described, for example, in the following patents: U.S. Pat. Nos. 5,549,111, 5,551,433, 5,555,534, 5,675,554, 5,685,308, 5,570,691, 5,581,517, and 5,617,862, the disclosures of which are incorporated herein by reference.

The transmit beamformer 14 includes a structure for generating a plurality of transmit waveforms. For example, the transmit beamformer 14 includes programmable waveform generators connected to digital to analog converters. Programmed digital waveforms are converted to analog signals. The analog signals are output to transmit amplifiers to generate excitation waveforms. Other analog or digital transmit beamformers may be used, including non-programmable waveform generators. The shape of the excitation waveforms is determined by the digital output from the programmable waveform generator. Preferably, the excitation waveforms comprise sinusoidal waves at a fundamental frequency modulated by a Gaussian envelope. Other excitation waveforms, such as unipolar or bipolar square or sinusoidal waves, may be used without any, with rectangular or with other shaped modulations.

The transmit beamformer 14 includes a plurality of transmit channels. For example, 32, 64, 128, or 256 transmit channels are provided. Each transmit channel is capable of generating an excitation waveform as discussed above. For example, each transmit channel includes a programmable waveform generator, a digital to analog converter, and a transmit amplifier. In other embodiments, various components are shared by a plurality of transmit channels.

The transducer 12 operatively connects to the transmit beamformer 14 and comprises an array of transducer elements. Each transducer element is substantially separated electrically and acoustically from other transducer elements. Any one or more of various transducers may be used, such as one dimensional linear or curved linear phased arrays. In other embodiments, the transducer 12 comprises a 1.5 dimensional or two-dimensional transducer array. The transducer 12 may comprise any number of transducer elements, such as 32, 64, 128, or 256. Other numbers of transducer elements may be used and may match, but preferably exceed the number of transmit channels.

Preferably, the transducer elements are spaced as a function of the wavelength associated with the highest operating frequency (transmit or receive frequency), such as the fundamental or a harmonic of the fundamental. For steered arrays, the transducer elements are preferably spaced by about ½ the wavelength of the highest operating frequency. In alternative embodiments, the spacing is about a quarter of a wavelength or 1 to 2 wavelengths. For a non-steered arrays, the spacing is about 1 wavelength of the receive frequency, but may be ½ or 2 to 4 wavelengths. Other spacings may be used.

The spacing is measured from the center of the transducer element to the center of another transducer element. The spacing of the adjacent transducer elements is said to be "about" a function of the wavelength of the receive frequency to account for manufacture tolerances, changes in transmit or receive frequencies within the transducer bandwidth, and other design choices.

The excitation waveforms from the transmit channels of the transmit beamformer 14 are provided to a respective plurality of transducer elements. In response to the excitation waveforms, the transducer elements generate acoustical energy. The acoustical energy is focused along one or more ultrasound scan lines as a function of various delays and apodizations relative to each excitation waveform. By varying the relative delays, acoustic energy may be sequentially or simultaneously generated along different scan lines. Any of various scan formats may be used, such as linear, curved linear, Vector®, sector, or other formats. The scan region may be responsive to a single possible aperture, such as transmitting from all or a subset of all the transducer elements for each transmit event. In alternative embodiments, a sliding or variable aperture associated with transmitting from different subsets of transducer elements for different transmit events may be used. As used herein, a single transmit event comprises transmitting excitation waveforms along one or more scan lines substantially simultaneously.

In one embodiment, the number of transmit channels equals the number of transducer elements. Alternatively, there are more or less transmit channels than transducer elements. Various of the embodiments described below may use all or only a sub-set of either or both the transmit channels or transducer elements.

Figure 2:
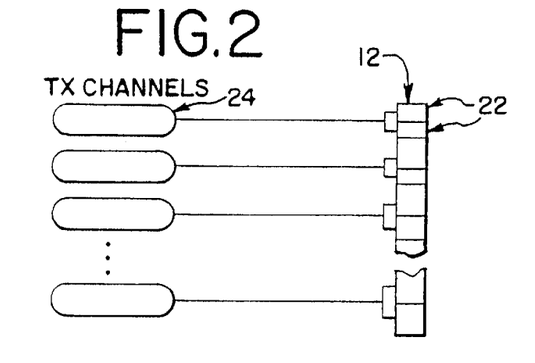
FIG. 2 is a graphical representation of connection between a plurality of transmit channels and a plurality of shorted transducer elements.

The number of transmit channels for use with any given aperture or set of transducer elements may be reduced by shorting two or more transducer elements together. Referring to FIG. 2, a representation of shorting pairs of adjacent transducer elements 22 to each transmit channel 24 is shown. Each pair of adjacent elements 22 are shorted to a single transmit channel 24, effectively forming one large element for beamformer purposes. The two elements 22 shorted together are excited at the same time by the same waveform generated by the transmit channel 24. Fewer transmit channels 24 may be used to obtain a same aperture width and an associated beamwidth as provided by twice the number of transmit channels 24. Other sets of elements 22 may be shorted together, such as shorting elements 22 separated by one or more additional elements, shorting inner and outer elements together and other configurations. More than two elements may be shorted together.

The elements 22 are shorted together by electrically connecting the elements 22. The electrical connection may be made using any of various techniques, such as connected with an electrical trace, switching structures, other circuitry, or multiplexer structures as discussed below.

Figure 6A:
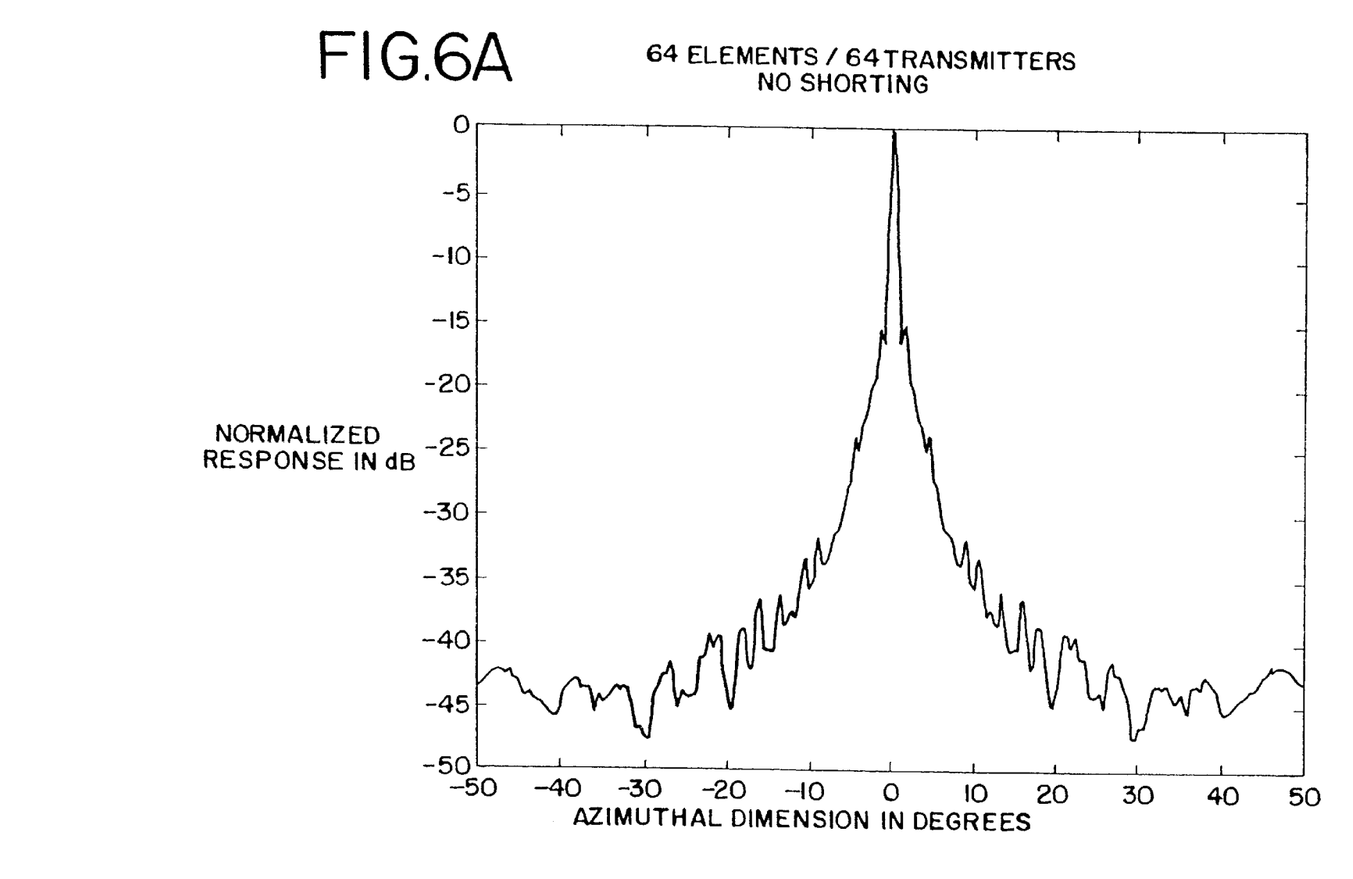
FIGS. 6A and 6B are graphical representations of one-way transmit beamplots.
Figure 6B:
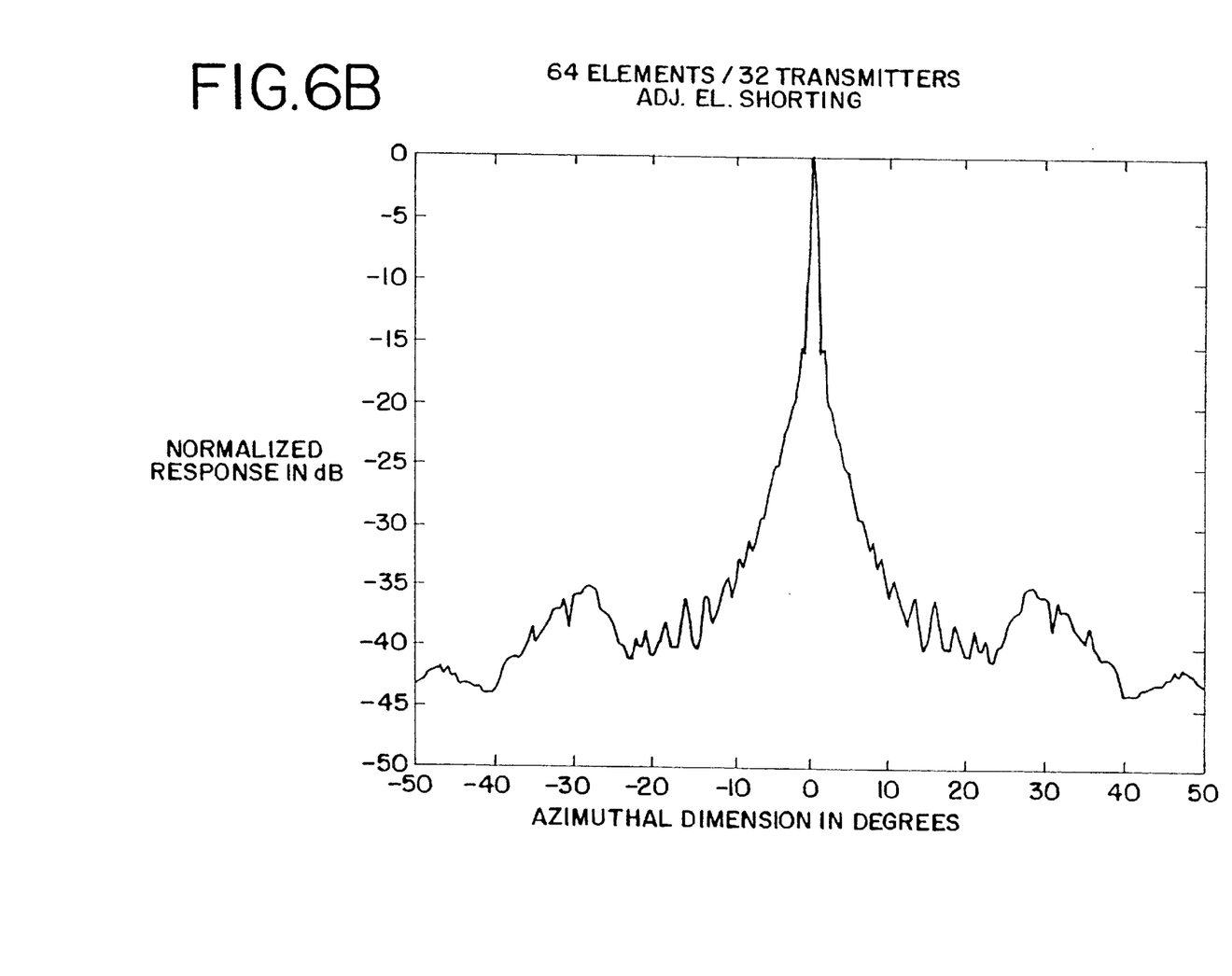

Referring to FIGS. 6A and 6B, one-way transmit beam plots using 64 separate single elements and adjacent element shorting of the 64 elements, respectively, are shown. In FIG. 6A, a 5 MHz transmit frequency with a 19 mm aperture using a 64 independently excited transducer elements is shown. The resolution is 2 mm at −6 dB. FIG. 6B shows a beam plot generated using the same aperture and 64 elements with half the number of transmit channels and adjacent element shorting at the 5 MHz fundamental transmit frequency. As is shown by a comparison of FIGS. 6A and 6B, the beamwidth and associated azimulthal resolution is similar.

If two or more elements 22 are shorted together, the power associated with the excitation waveform generated by the transmit channel 24 is preferably increased. In one embodiment, the current output by each transmit channel is doubled for shorting two elements 22 together. Where possible, the current output is changed, such as changing the amplitude output from the programmable waveform generator. Alternatively, an output gain stage is designed to have increased output power for the same or a different excitation signal. The power supply driving the transmit channel is also changed to provide the increased power. The output current of the transmitter channel 24, when connected to two transducer elements 22 in parallel, may be doubled without exceeding any limits on the acoustic power when compared to using two transmit channels 24 connected to respective two transducer elements 22. The peak to peak output voltage swing of the excitation waveform is a function of the output current of the transmit channel 24 and the load impedance of the transducer elements 22. Shorting together adjacent transducer elements 22 cuts the load impedance in half. Therefore, twice as much current may be output by the transmit channel for a pair of shorted elements than for a pair of transmit channels 22 connected to a respective pair of transducer elements 22, without exceeding the breakdown voltage. Each of the shorted transducer elements 22 will conduct half the total current output by the transmit channel 24. Therefore, a single transmit channel 24 may drive two transducer elements 22 to generate substantially the same acoustic signal power as two transmit channels separately driving the same two transducer elements.

Since it is often more practical to design the transmit channel 24 with a high output current capability than a high output voltage capability, shorting the elements 22 together and driving them from a single high current output transmit channel 24 is a cost effective method to increase transmitted acoustic power.

Increasing the power of the excitation waveforms output by the transmit channels 24 to the shorted transducer elements 22 provides a substantially similar acoustic output power generated by twice the number of transmit channels 24 connected to non-shorted transducer elements 22. By reducing the number of transmit channels 24, the cost of the associated transmit beamformer 14 (FIG. 1) may be reduced. In alternative embodiments, the number of transmit channels 24 and/or the output of the power supply and each associated transmit channel 24 is increased to increase the transmit acoustic power. Preferably, the power associated with the excitation waveform does not exceed the breakdown voltage of any of the components within the transmit channel 24, such as capacitors, resistors, and transistors.

The transmitted acoustic energy propagates through the target, and some of the acoustic energy is reflected back towards the transducer 12. Using the same or different transducer elements 22, the reflected acoustic energy is converted into received electrical signals.

The received electrical signals are provided to the receive beamformer 20. The receive beamformer 20 preferably includes a plurality of receive channels. In one embodiment, each receive channel includes an amplifier for amplifying the received electrical signals. The amplified signals are digitized and delayed for each receive channel relative to the other receive channels. The delayed signals are summed together to form a coherent signal. Other receive beamformers and associated receive channels may be used, such as analog receive beamformer systems.

Each receive channel may be associated with one or more transducer elements 22. For example, no shorting of transducer elements is provided for receiving reflected acoustic energy. In alternative embodiments, the same or different groupings or shorting of the elements 22 is used for reception as is for transmission of acoustic energy.

The coherent signal is filtered to obtain ultrasound data at a desired frequency, such as the fundamental or a harmonic frequency. As used herein, a fundamental or harmonic frequency includes a band of frequencies centered around the particular fundamental or harmonic frequency. Also as used herein, harmonic is intended broadly to include any one of various higher harmonics (e.g., two or three times the fundamental frequency at which the transmit beam is centered). For example, a band pass filter is used to obtain information at a second harmonic frequency. Filtering may also be implemented using demodulation to a baseband frequency, such as 0 Hz, and low pass or bandpass filtering to isolate information at or near the baseband frequency. The filtered signals may be processed to generate an analytical lines with synthetic line interpolation as discussed in U.S. Pat. Nos. 5,623,928, 5,667,373 and 5,793,701.

In one preferred embodiment, the coherent signals are filtered to obtain information associated with a harmonic frequency of the fundamental transmit frequency, such as the second harmonic. A filter may be used in the receive beamformer or at other locations in the ultrasound system. Through non-linear propagation, harmonics of the fundamental transmit frequency are generated. Images may be formed from information generated by these non-linear processes. These images display increased resolution and decreased clutter. Imaging using harmonic information may also minimize artifacts generated by grating lobes generated from transmitting from shorted or spaced elements.

The harmonic imaging techniques described above can be used for both tissue and contrast agent harmonic imaging. In harmonic imaging of tissue, no additional contrast agent is added to the target, and only the non-linear characteristics of the tissue are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible. In this case, no contrast agent is introduced into the tissue at any time during the entire imaging session.

In contrast agent harmonic imaging, any one of a number of known ultrasound contrast agents generating increased non-linear response, such as microspheres or the FS069 agent by Schering of Germany, is added to the target or subject in order to enhance the non-linear response of fluid. The contrast agents radiate ultrasonic energy harmonics of an insonifying energy at fundamental frequencies.

The ultrasound data, either at a harmonic or fundamental frequency, is output by the receive beamformer 20 to the image processor 16. The image processor includes a B-mode and/or a Doppler processor. For B-mode processing, the signals are detected and logarithmically compressed. For Doppler processing, an estimate of the velocity of a target is generated. In addition to velocity estimates, acceleration and energy estimates may also be generated. The Doppler processor may also generate spectral Doppler strip information. The output data of the B-mode and/or Doppler processors is provided to a scan converter. The scan converter converts the polar coordinate output data to Cartesian coordinate data for display on a monitor. The display includes one of or a combination of B-mode and Doppler information.

Shorting adjacent elements 22 and using harmonic receive processing may be used to acquire information representing the motion of tissue, such as using Doppler techniques as disclosed in U.S. Pat. No. 5,285,788. the disclosure of which is incorporated herein by reference.

In one preferred embodiment, a switching structure is used to allow for a variable aperture. In this embodiment, different transducer elements may be shorted together or spaced transducer elements may be used for generating acoustical energy with fewer transmit channels or receiving acoustical energy with fewer receive channels.

Figure 3:
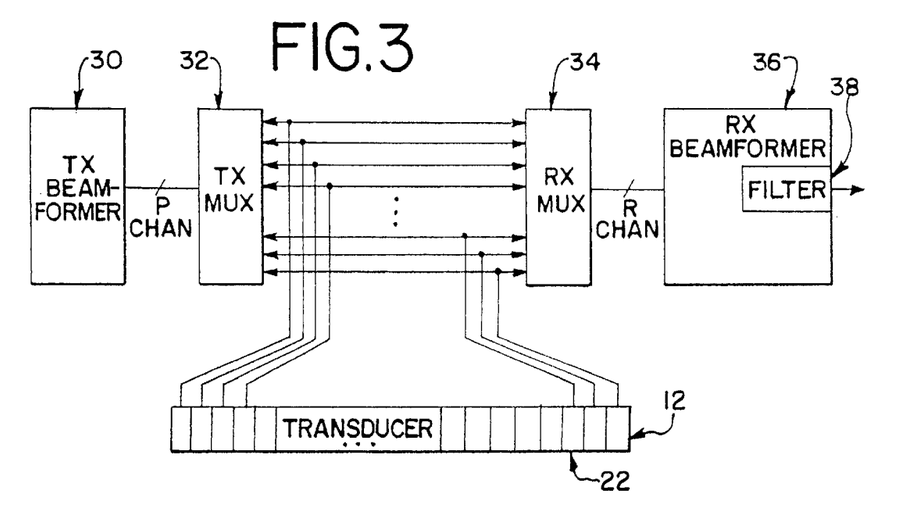
FIG. 3 is a block diagram representation of a multiplexer structure for performing the shorting as represented by FIG. 2.

Referring to FIG. 3, a schematic block diagram of a transmit and receive structure for using a variable aperture is shown. A transmit beamformer 30 connects to a transmit multiplexer 32. Preferably, the transmit multiplexer comprises high voltage FET switches. A receive multiplexer 34 connects to a receive beamformer 36. Preferably, the receive multiplexer 34 comprises high voltage diode switches, such as disclosed in U.S. Pat. No. 5,617,862. The receive beamformer 36 includes a filter 38. The transducer 12 and the associated array of elements 22 are each independently electrically connectable to both the transmit beamformers 30 and the receive beamformer 36. A plurality, P, of transmit channels, M, within the transmit beamformer 30 connect to the transmit multiplexer 32. Likewise a plurality, R, of receive channels of the receive beamformer 36 are connected to the receive multiplexer 34. P may equal R, but more or fewer transmit or receive channels may be used. In one embodiment, the transmit and receive structure of FIG. 3 comprises the variable aperture system disclosed in U.S. Pat. No. 5,617,862, the disclosure of which is incorporated herein by reference. Other multiplexer or switching networks may be used.

Using the transmit multiplexer 32, the P transmit channels or a subset of the P transmit channels may be operatively connected to different elements 22 of the transducer 12. By switching which elements 22 are connected to the P or a subset of the P transmit channels, the aperture used may be varied. For example, P=64 transmit channels for connection with various ones of a 128 elements 22. The 64 transmit channels may be operatively connected through the transmit multiplexer 32 to different groupings of the transducer elements 22 for different transmit events. In one embodiment for imaging with a synthetic aperture, the 64 transmit channels are connected to the leftmost transducer elements 22. Excitation waveforms with appropriate delays are used to generate acoustical energy focused at an area within the target. After reflected acoustic energy is received along a portion or the entire range of interest of the scan line, the transmit multiplexer 32 operatively connects the 64 transmit channels to the right most transducer elements 22. The focus and delay profiles of the excitation waveforms are altered in order to image the same area of the target as was imaged with the excitation waveforms of the left half of the transducer 12. Receive signals associated with the scan lines generated by the left half and the right half of the transducer 12 are combined to generate a composite scan line, such as by adding the scan line data prior to detection. This process is disclosed in U.S. Pat. Nos. 5,623,928, 5,667,373 and 5,793,701, the disclosures of which are herein incorporated by reference. This process is repeated in order to scan a plurality of focal areas within a region of the target. In alternative embodiments, the synthetic aperture comprising all the elements 22 of the transducer 12 is used in different ways than the right half and left half division, such as using every odd transducer element 22 and then every even transducer element 22, using inner and outer subsets of transducer elements 22 or other divisions. Other receive aperture configurations are possible, including using the same configurations and associated switching as the transmit aperture configurations discussed herein.

Using the variable aperture to generate composite information as discussed above may be used where elements 22 are shorted together. For example, 32 transmit channels may be connected to 64 transducer elements 22. Preferably, adjacent elements 22 are shorted together by switching a single transmit channel in the transmit multiplexer 32 to two adjacent transducer elements 22. In alternative embodiments, the 32 transmit channels are connected to every other transducer element without any shorting. Connecting the transmit channels to every other element or shorting adjacent pairs of elements effectively makes the elements more spaced, creating grating lobes. The receive aperture configuration may be the same or different than the transmit aperture configuration. To minimize the effect of grating lobes, the receive beamformer 36 and the filter 38 obtains and isolates ultrasound data associated with a harmonic of the fundamental transmit frequency. The various aperture combinations discussed above may be used in this embodiment.

Figure 7:
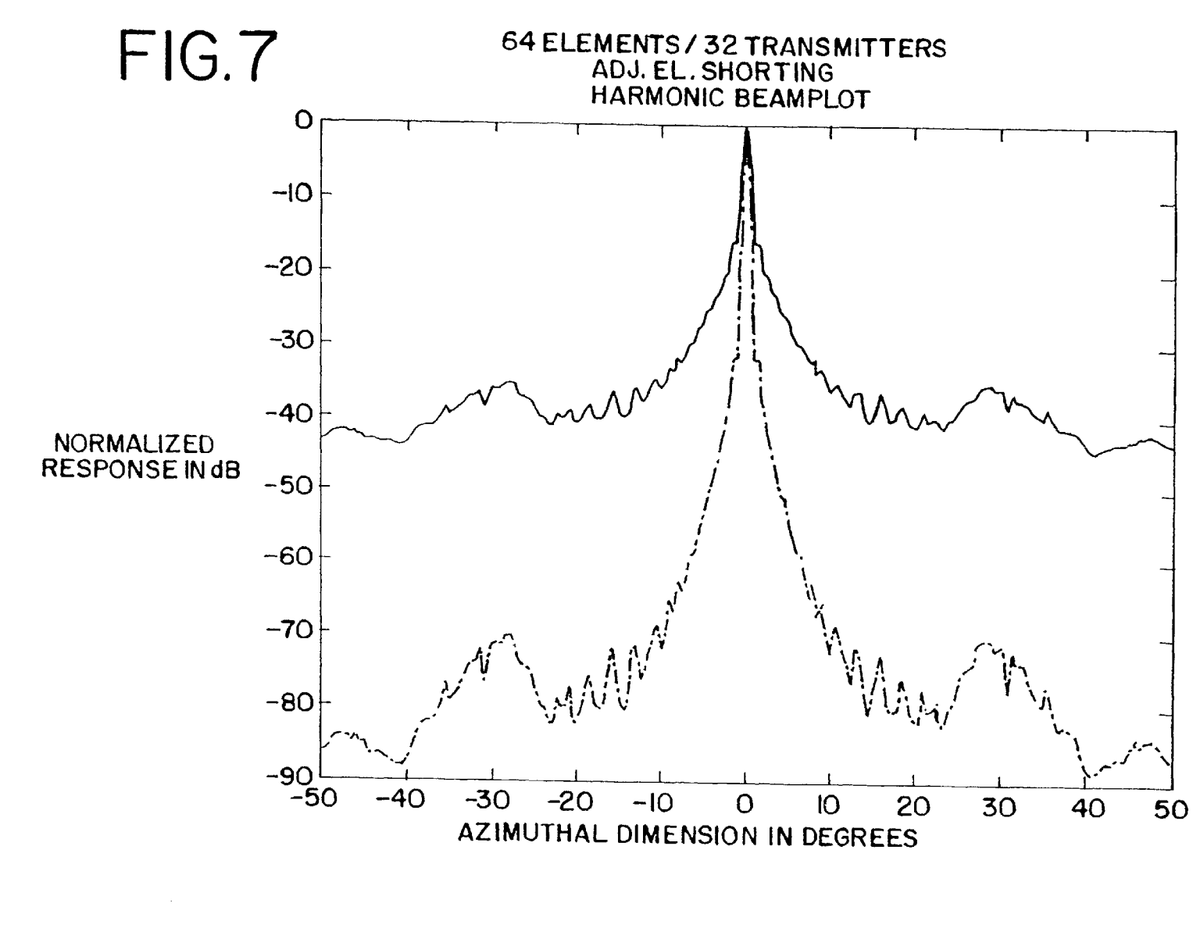
FIG. 7 is a graphical representation of a two-way transmit and receive beamplot using a left-right grouping of transducer elements.

Referring to FIG. 7, the one-way azimulthal response associated with transmission by 32 transmit channels connected to 64 adjacent elements 22 is shown. The solid line represents the one-way response at the fundamental transmit frequency with adjacent element shorting. The dashed line represents the one-way response at the second harmonic of the fundamental frequency.

In one embodiment, left-right synthesis or combination of apertures is provided. In alternative embodiments, the inner 64 elements 22 comprise one aperture and two subsets of 16 outer elements 22 comprises a second aperture. Other aperture configurations for generating synthetic scan line data may be used.

In alternative embodiments, the transmit multiplexer 32 and/or the receive multiplexer 34 are used to generate a sliding variable aperture. A subset of the total number of elements 22 is operatively connected to the transmit channels 24. After one or more transmit events, the aperture is adjusted or slid to different elements 22. For example, the transmit multiplexer 32 slides the aperture in steps of one or more transducer elements (i.e. transducer elements 0 through 7 are connected for one transmit event and transducer elements 1 through 8 are connected for a second transmit event). More or fewer transducer elements and transmit channels may be used.

Figure 4A:
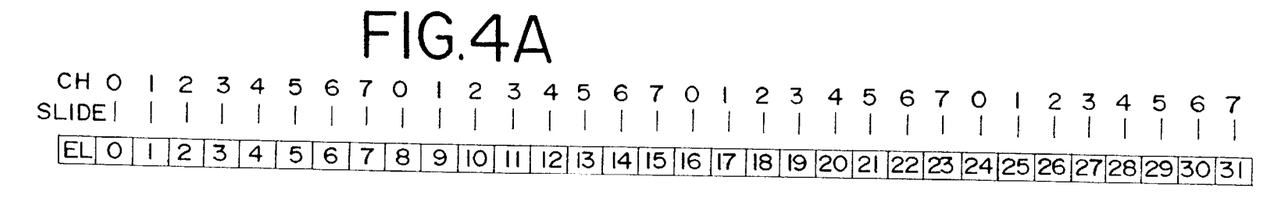
FIGS. 4A–D are representations of various switchable apertures for use with the multiplexer structure of FIG. 3.
Figure 4B:
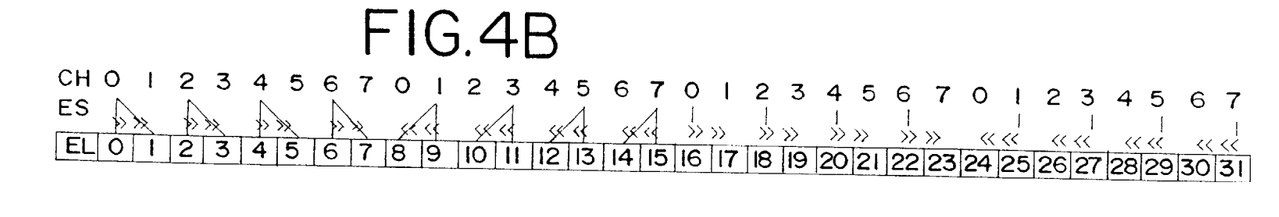
Figure 5:
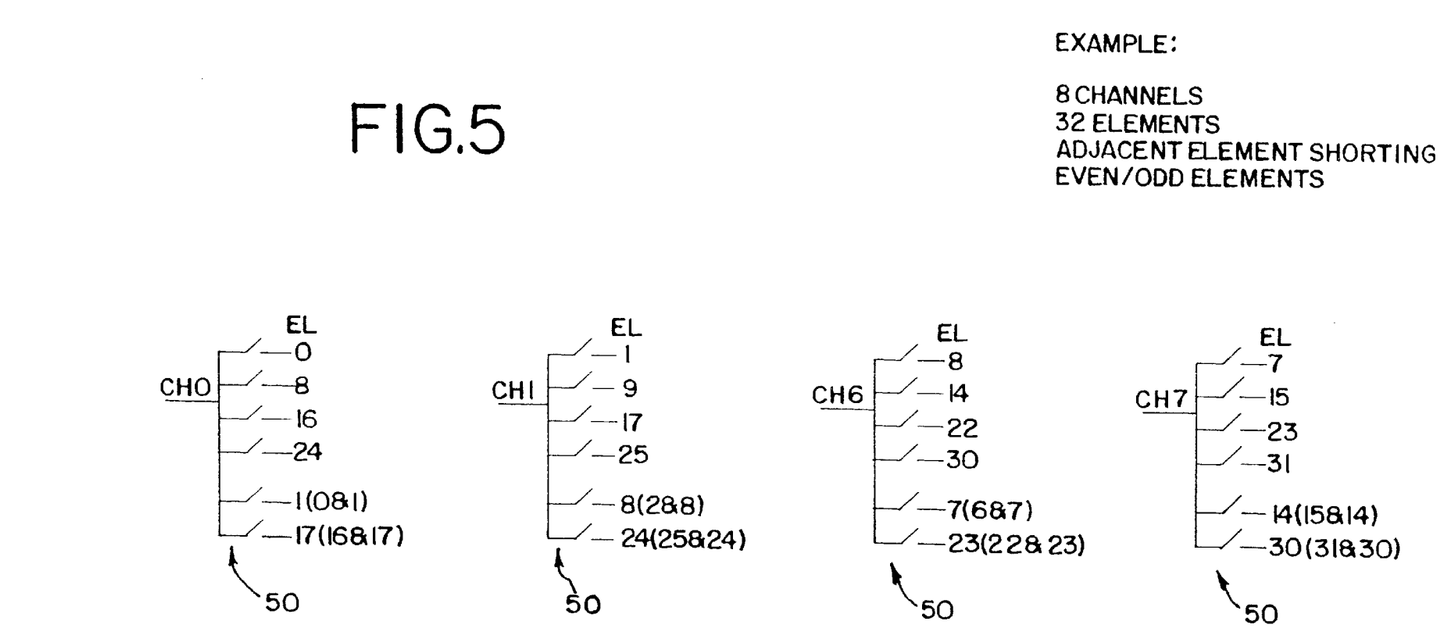
FIG. 5 is an electrical schematic representation of the multiplexer connections between transmit channels and transducer elements for FIG. 3.

Referring to FIG. 5, an electrical schematic for implementing the transmit multiplexer 32 and/or the receive multiplexer 34 to connect the transmit or receive channels and associated transducer elements shown in FIGS. 4A and B is shown. The transmit or receive multiplexers 32 or 34 comprise a single layer of multiplexers or switching networks 50. One multiplexer 50 is provided for each channel. Given P transmit channels 24, each transmit channel numbered M (0 through P−1) is connectable through the multiplexer 50 to a transducer element of the same number M, element number P+M, element number 2×P+M, element number 3×P+M . . . . This structure provides for a sliding aperture. The number of transducer elements 22 is preferably a multiple of the number of transmit channels P, such as 2P, 3P, 4P, . . . . If the number of transducer elements is 2P and the number of transmit channels is P or fewer, 2P switches are required to ensure that each transducer element 22 may be connected to a transmit channel.

In one embodiment represented by FIG. 4A, 8 transmit channels, labeled channel 0 through channel 7, are provided for switchable connection to 32 transducer elements, labeled element 0 through element 31. A sliding aperture of 8 elements using all the elements 0 through 31 may be defined by 32 switches. In this embodiment, transmit channel 0 is connectable to element 0, element 8, element 16 and element 24. Likewise channel 1 is connectable to element 1, element 9, element 17, and element 25. This pattern continues for the remaining transmit channels. One aperture is defined by connecting channels 0 through 7 to respective elements 0 through 7. To vary the aperture or slide the aperture by one element, channel 0 is connected to channel 8. The remaining channels 1 through 7 are still connected to the respective elements 1 through 7. The aperture is moved one step to the right. Preferably, the transmit beamformer 30 and the associated transmit channels 24 account for the various switching connections to provide the appropriate delay and apodized excitation waveforms to the connected transducer elements. The waveform may vary from element to element.

To provide for adjacent element shorting, shorting of two or more elements together or transmission or reception from spaced elements, such as even or odd numbered elements, additional switches are provided on each multiplexer 50. For even numbered transmit channels M (e.g. 0, 2, 4 . . . . ), these additional switches are provided to connect the channel M to transducer elements M+1, 2×P+M+1, 4×P+M+1 . . . . For each odd numbered transmit channel M, electrical switches for connection to the transducer elements P+M−1, 3×P+M−1, 5×P+−1. . . . are provided as shown in FIG. 5. In the example represented in FIGS. 4 and 5, channel 0 may be additionally connectable to elements 1 and 17. Channel 1 is additionally connectable to elements 8 and 24. The pattern continues through channel 7 as shown, which is connectable to additional elements 14 and 30. Other patterns may be used, such as connecting Channel 1 to elements 1 and 0, Channel 3 and elements 3 and 2, and so on (i.e. reverses the connections discussed above).

These additional switches within the multiplexers 50 allow for various aperture configurations. For example adjacent element shorting is provided as shown in FIG. 4B. Each transmit channel M is connected to two adjacent transducer elements. Transducer elements 0 and 1 are connected to transmit channel 0, transducer elements 2 and 3 are connected to transmit channel 2, and so on as shown. Using the multiplexers 50 shown in FIGS. 4B and 5, fewer switches than 2 times the number of transducer elements designate an aperture. Fewer switches may provide a more efficient implementation. In particular, a number of switches that is only 1.5 times the total number of transducer elements are operable to designate an aperture of adjacent shorted elements which can slide across the array. To slide the aperture, channel 0 is connected to elements 16 and 17. Steps associated with a greater number of transducer elements may be used. The aperture for adjacent shorted elements is 16 elements wide using only 8 transmit or receive channels.

Figure 4C:
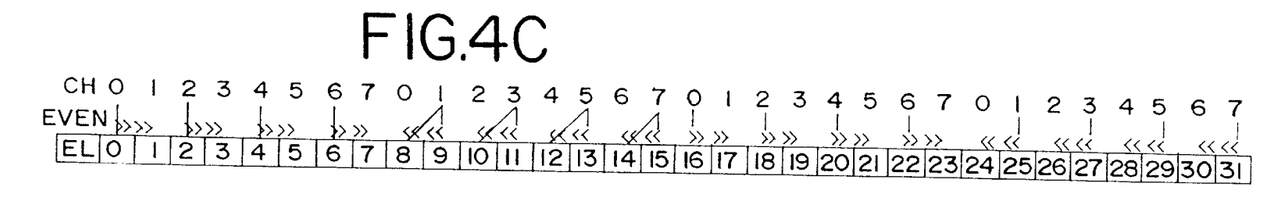
Figure 4D:
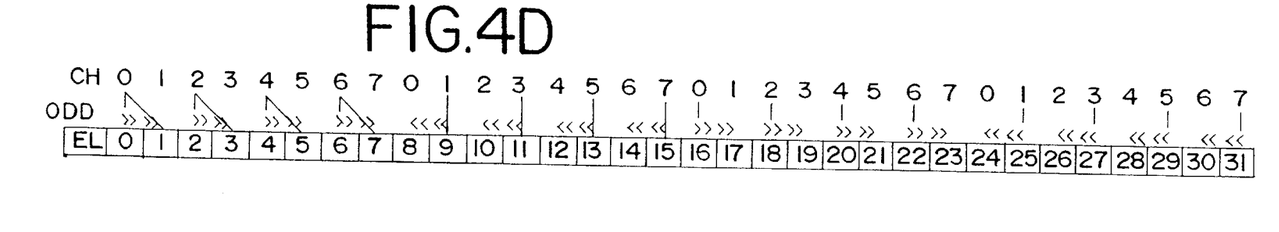

Using the same multiplexers 50 shown in FIG. 5, various other apertures may be used for transmission or reception. For example, the 8 transmit channels may be connected to even transducer elements as shown in FIG. 4C, or to odd transducer elements as shown in FIG. 4D. These connections comprise a subset of the connections shown in FIG. 4B. Likewise and as shown in FIG. 4D the aperture defined by odd numbered transducer elements is a subset of the aperture shown in FIG. 4B. These even or odd transducer element array apertures may also be slid across the full transducer array. Preferably, harmonic receive processing is also used for the apertures shown in FIGS. 4C and 4D. In alternative embodiments, the multiplexers 50 of FIG. 5 are used to designate a single arbitrary aperture for all transmit and/or receive events (i.e. non-sliding), an aperture for any of the combinations discussed above, or any other moving or non-moving aperture, including any sub-set or all of the transducer elements.

By providing the various aperture configurations as discussed above with the multiplexers 50, each excitation waveform only passes through one switch between the transmit channel and the transducer element. Likewise, the received signal only passes through one switch between the receive channel and the transducer element. Therefore, alterations to the excitation waveforms or receive signals caused by switching structures and timing adjustments associated with a multiple layer switching structure are avoided.

The receive multiplexer 34 of FIG. 3 may comprise the same multiplexer structure as represented in FIGS. 4 and 5. In alternative embodiments, the transmit and receive multiplexers 32 and 34 comprise different structures. In one embodiment, the receive channels of the receive beamformer 36 operatively connect to the same transducer elements as respective transmit channels of the transmit beamformer 30. In alternative embodiments, twice as many receive channels are used, so that transducer elements 22 are not shorted together or spaced apart for receive processing. In yet other alternative embodiments, fewer receive channels are used, such as shorting adjacent elements 22 to respective receive channels and connecting a greater number of transmit channels to non-shorted and non-spaced transducer elements 22.

Figure 8A:
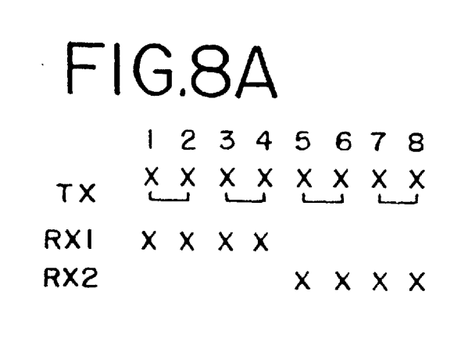
FIGS. 8A–8C are representations of various switchable apertures.
Figure 8B:
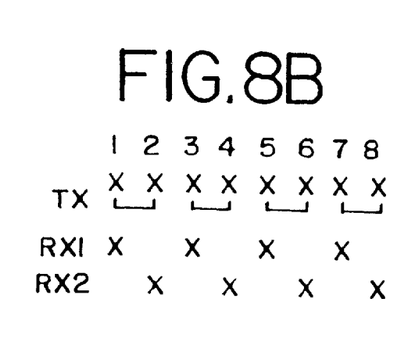
Figure 8C:
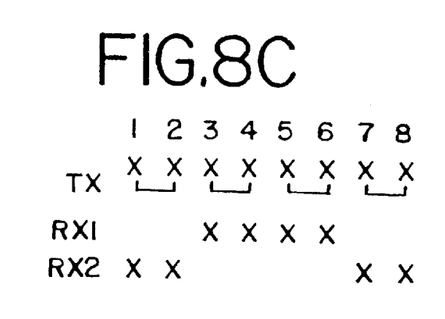

Referring to FIGS. 8A through 8C, various switchable aperture configurations for transmit and receive processing are shown. The aperture configuration for transmit processing is represented by "TX," and the aperture configuration for receive processing is represented by "RX." Shorting as discussed above is represented by a bracket connecting elements "x". The transmit aperture configurations shown may be implemented using 1.5N switches, such as using the multiplexer described above, where N is the number of transducer elements. The receive aperture configuration of FIG. 8B preferably also uses 1.5N switches. The receive aperture configurations of FIGS. 8A and 8C may use 1N switching, such as connecting one channel to one element. More switches may be used for any of the transmit or receive configurations.

Multiple transmit or receive events may be used. For example and referring to FIG. 8A, the acoustic energy is transmitted twice using the configuration represented by TX. For the first transmit event, the receive configuration represented by RX1 is used. For the second transmit event, the receive configuration represented by RX2 is used. Other configurations on transmit or receive, with or without multiple transmit or receive configurations, and with or without element shorting or spacing, may be used. Eight elements are shown for convenience, and the aperture may comprise more or fewer elements.

Figure 9:
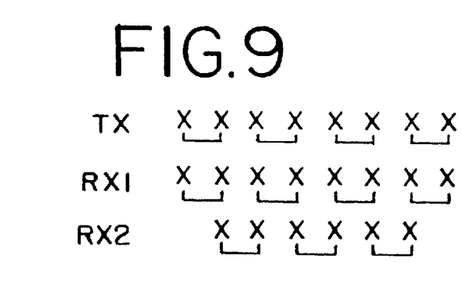
FIG. 9 is a representation of a switchable apertures.

Referring to FIG. 9, an additional switchable aperture scheme is shown using the representations discussed above. The implementations shown in FIG. 9 may require additional switches, such as 2N switches, to implement the receive aperture configuration. For 2N switches, each odd channel is connectable to elements M, M+1, M−1, P+M, P+M−1, P+M+1, 2P+M, 2P+M−1, 2P+M+1 . . . . Each even channel is connectable to elements M, M+1, M−1, P+M, P+M+1, P+M1, 2P+M, 2P+M−p1, 2P+M+1. . . .

Figure 10:
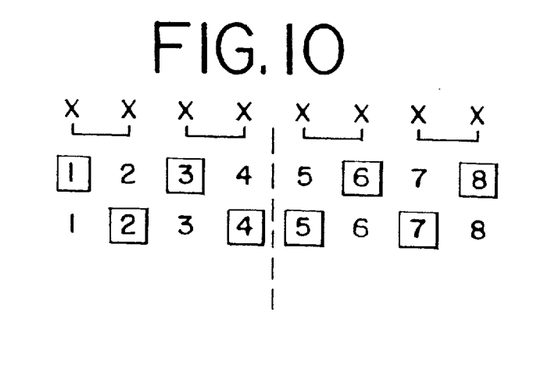
FIG. 10 is a representation of a switchable aperture.

Referring to FIG. 10, an aperture configuration requiring only 1N switches for the receive aperture configuration is shown. Using a 1N switching structure discussed above, elements 1–8 may be connected to respective receive channels 14. The receive aperture comprises a mirror image about the center of the aperture, allowing for fewer switches.

Referring to FIGS. 8A–8C, 9 and 10, other combinations of elements with shorting or spacing for transmit and/or receive are possible. These figures represent a few possible combinations.

By providing a multiplexer or other structure for transmitting or receiving from spaced elements or shorted elements, fewer transmit and/or receive channels may be used. By reducing the number of transmit and/or receive channels, the cost of an ultrasound system may be decreased. The grating lobes and associated artifacts resulting from shorting transducer elements together or transmitting from spaced transducer elements may be reduced by using harmonic information for imaging. Furthermore, the multiplexer structure described above may be used for generating any one of various apertures associated with no element shorting.

As discussed above, different aperture techniques may be used for implementing transmit apertures than for implementing receive apertures. Using a different aperture technique for transmit and receive operations allows for minimizing grating lobes. More versatile imaging or larger apertures may be provided using these techniques for systems with fewer transmit or receive channels than the number of transducer elements, such as inexpensive systems with only 32, 64 or 128 channels.

Using versatile multiplexers, different configurations are used for transmit and receive events. Such multiplexers are discussed above and in U.S. Pat. No. 5,617,862, the disclosure of which is incorporated herein by reference. Other multiplexers may be used. The multiplexers are controlled independently for transmit and receive events to provide the differing aperture techniques.

The aperture techniques include synthetic aperture, shorting elements, skipping elements and sliding aperture techniques. These techniques result in different types of apertures. For example, the shorting element technique provides an aperture where two or more transducer elements are shorted to the same transmit or receive channel. The skipping elements technique provides for a sparse aperture where one or more elements are not connected to transmit or receive channels but elements on each side of the non-connected element are connected to respective transmit or receive channels. The synthetic aperture technique provides for reception with two different apertures, such as right and a left half of the array apertures. The sliding aperture technique provides for an aperture that moves across the array of elements as a function of transmit or reception event.

In one embodiment, the shorting element technique is used for the transmit aperture and the synthetic aperture is used for the receive aperture. FIG. 8A shows one representation for this combination of aperture techniques. For a transmit event, adjacent elements of the transmit aperture are shorted to common transmit channels. For the synthetic aperture receive technique, ultrasonic energy is transmitted at least twice. For each transmission, a different receive aperture is used, such as the right half and left half apertures shown. Other split receive apertures may be used for the synthetic aperture technique, such as the apertures shown in FIGS. 8B, 8C, 9 and 10.

Figure 11A:
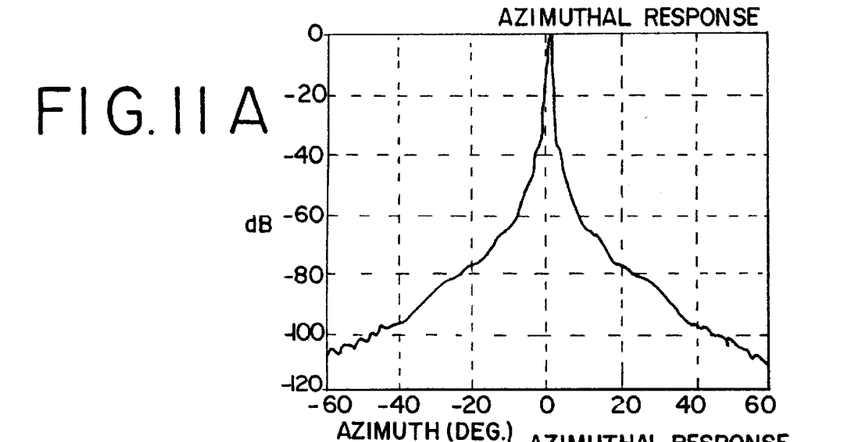
FIGS. 11A–C are graphical representations of two-way transmit and receive beamplots.
Figure 11B:
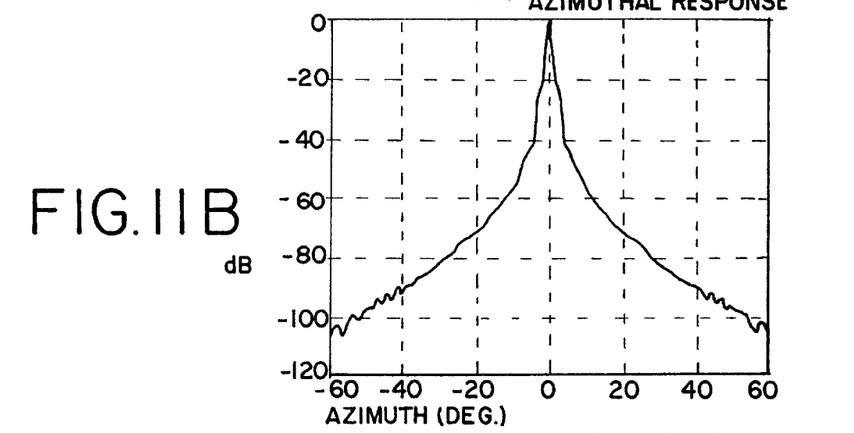
Figure 11C:
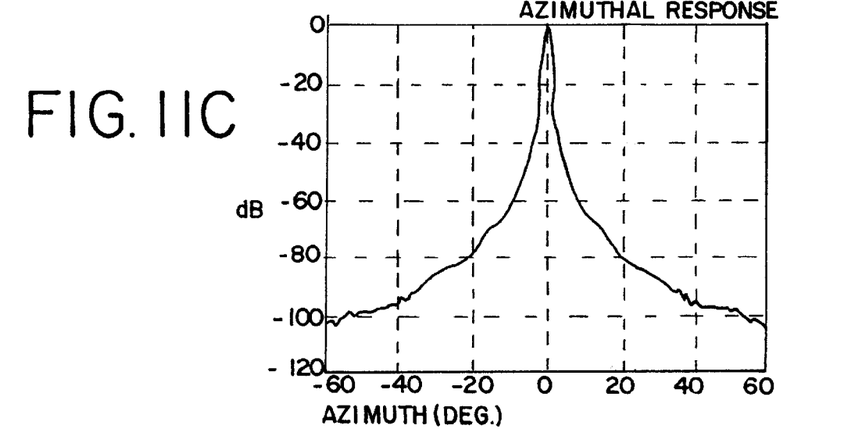

Using the techniques represented by FIG. 8A, larger apertures and associated increased resolution are provided. The two-way resolution is determined by the total transmit and receive apertures. FIG. 11A represents the normalized azimuthal response of a 19 mm array with 64 elements where the transmit and receive apertures include 64 channels connected with 64 elements, respectively. FIG. 11B shows the normalized azimuthal response obtained using 32 continuous (i.e. neighboring) elements of the 64 element array with 32 channels, respectively, for transmitting ultrasonic energy and using 32 channels sequentially connected to different groupings of elements for receiving echoes using the synthetic aperture technique. A wider response is obtained for the arrangement associated with FIG. 11B than for the arrangement associated with FIG. 11A. FIG. 11C shows the normalized azimuthal response for the arrangement of FIG. 8A using 64 elements and only 32 channels. The azimuthal response shown in FIG. 11C is similar to the response shown in FIG. 11A, but is obtained using half the number of transmit and receive channels.

Figure 12:
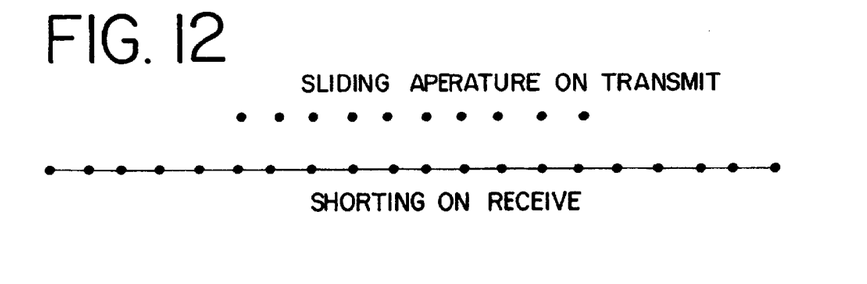
FIG. 12 is a representation of a switchable aperture.

In another embodiment shown in FIG. 12, the sliding aperture technique is used for the transmit aperture and the shorting element technique is used for the receive aperture. For each transmit event, the aperture is slid or moved by one or more elements along the array of elements. Echo signals responsive to each transmit event are received with the receive aperture. The receive aperture comprises a plurality of sets of adjacent elements shorted to common receive channels as shown. Different groupings of shorted elements may be provided, including a receive aperture using fewer or more elements. The shorting element technique for the receive aperture allows for a greater frame rate than the synthetic aperture technique.

Figure 13:
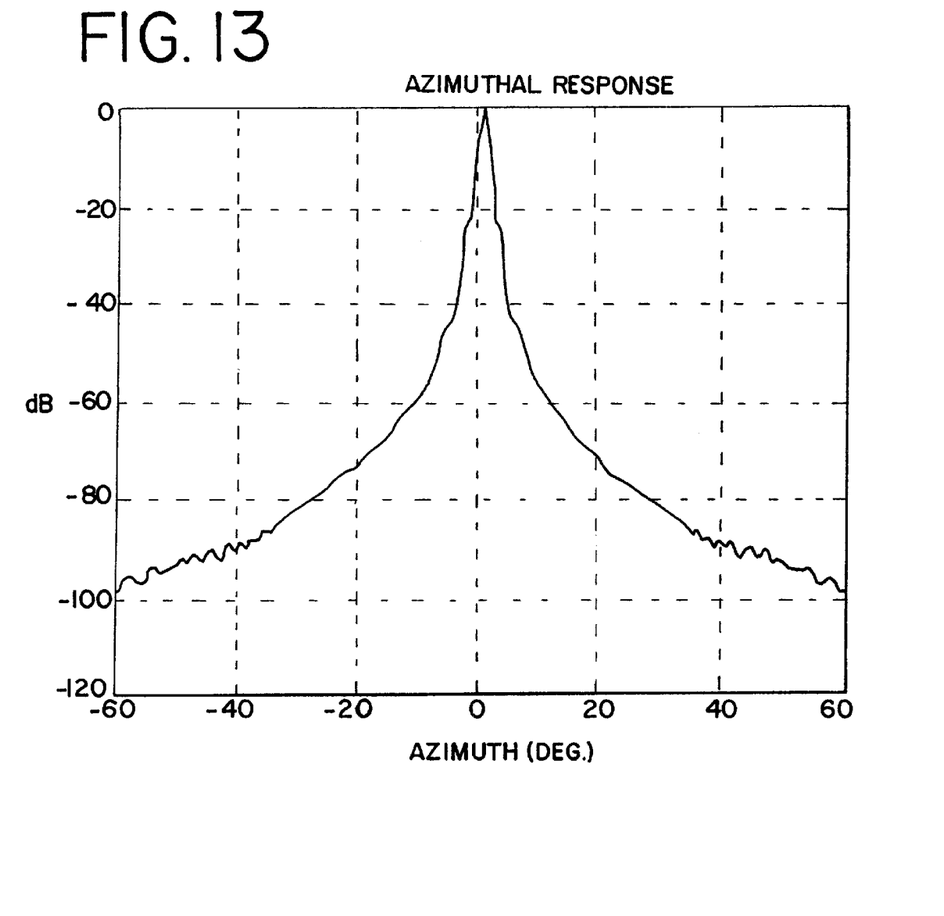
FIG. 13 is a graphical representation of a two-way transmit and receive beamplot responsive to the apertures shown in FIG. 12.

FIG. 13 represents the two-way normalized azimuthal response corresponding to the transmit and receive aperture techniques of FIG. 12. A 19 mm array with 64 elements is modeled where the sliding aperture is 32 elements wide and the shorted receive aperture is 64 elements wide. A response similar to the response represented by FIG. 11B is provided (i.e. about 2.05 degrees at the −6.0 dB width).

Figure 14:
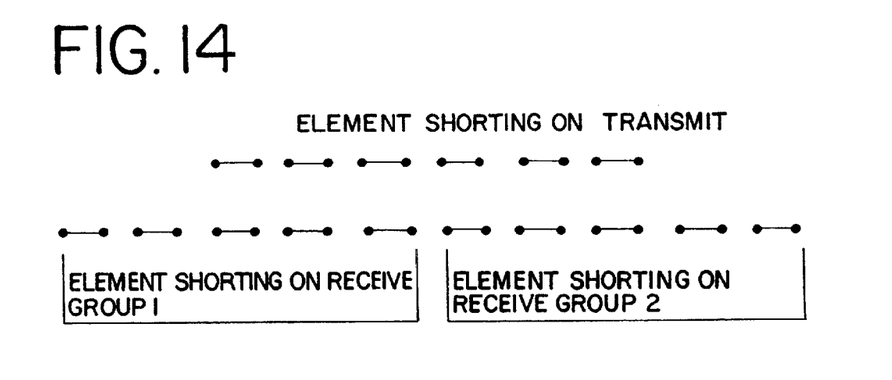
FIG. 14 is a representation of a switchable aperture.

In another embodiment shown in FIG. 14, the shorting element technique is used for the transmit events and the shorting element technique is used with the synthetic aperture technique for the receive events. The receive aperture comprises left and right half apertures responsive to the synthetic aperture technique. Each left and right half aperture comprises a plurality of pairs of adjacent elements shorted to receive channels. A large effective aperture is provided with a minimum of channels by combining synthetic aperture and shorting element techniques.

Figure 15:
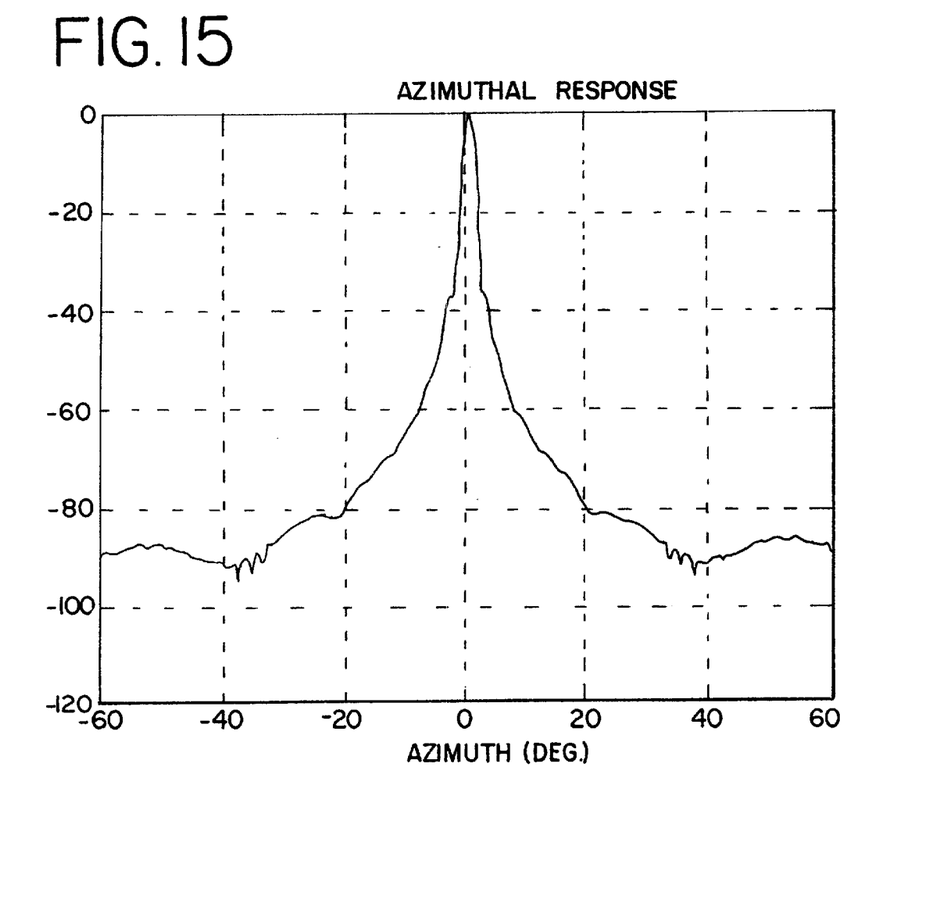
FIG. 15 is a graphical representation of a two-way transmit and receive beamplot responsive to the apertures shown in FIG. 14.

FIG. 15 represents the two-way normalized azimuthal response corresponding to the transmit and receive aperture techniques of FIG. 14. A 19 mm array with 64 elements is modeled where the transmit aperture is 64 elements wide with 32 channels shorted to adjacent elements and the total effective receive aperture using 16 channels is 64 elements wide. At −6.0 dB, the width of the response is about 1.71 degrees, but grating lobes at about 50 degrees are generated.

Figure 16:
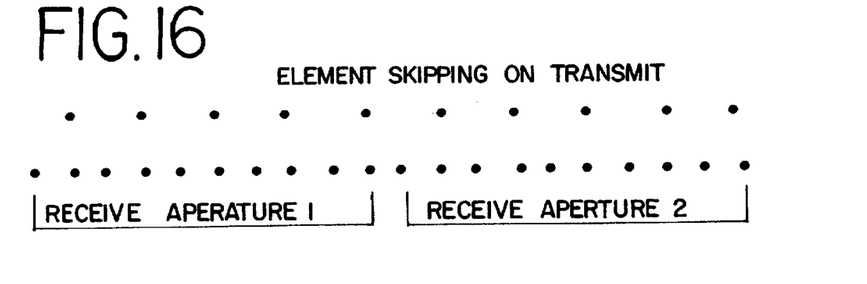
FIG. 16 is a representation of a switchable aperture.

In yet another embodiment shown in FIG. 16, the skipping element technique is used for the transmit events and the synthetic aperture technique is used for the receive events. Every other element is used for the transmit aperture. Other element spacing may be provided. The synthetic aperture technique component apertures shown comprise left and right half apertures, but other component apertures may be provided, such as providing a first component aperture associated with even elements and a second component aperture associated with odd elements.

Figure 17:
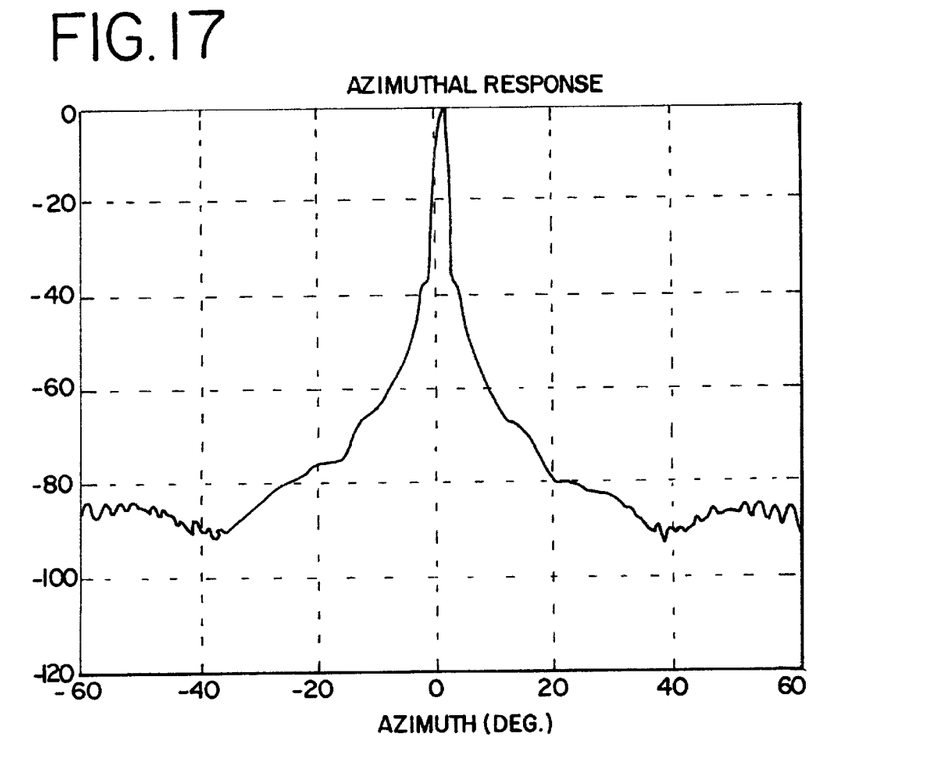
FIG. 17 is a graphical representation of a two-way transmit and receive beamplot responsive to the apertures shown in FIG. 16.

FIG. 17 represents the two-way normalized azimuthal response corresponding to the transmit and receive aperture techniques of FIG. 16. A 19 mm array with 64 elements is modeled where the transmit aperture is 64 elements wide and the total effective receive aperture is 64 elements wide. At −6.0 dB, the width of the response is about 1.71 degrees, but grating lobes at about 50 degrees are generated.

Figure 18:
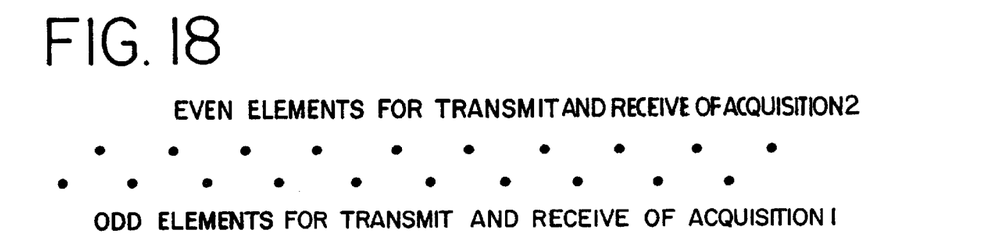
FIG. 18 is a representation of a switchable aperture.

Other combinations are possible. For example, FIG. 18 represents using the skipping element technique for the transmit and receive events. The synthetic aperture technique is used for combining even and odd spaced skipping element receive apertures. In this embodiment, the transmit aperture is altered for each of the receive partial apertures. In a first transmit and receive sequence, odd elements are used. In a second transmit and receive sequence, even elements are used. The received data is used to generate a synthetic aperture. The azimuthal response is the same as transmitting from and receiving from all elements. However, fewer channels are required but at a lower frame rate.

Yet another combination is represented in FIG. 10. The shorting element technique is used for transmit events. A combination of the synthetic aperture and skipping element techniques are used for receive events. In this embodiment, the component apertures of the synthetic aperture comprise skipped element groupings that are symmetrical about a center of the elements. In alternative embodiments, other equal or unequal spaced groupings may be used. For example, one component aperture comprises every odd element and the other component aperture comprises every even element. The azimuthal response of this alternative is similar to the response obtained using the aperture configurations shown in FIGS. 8A, 8B, and 8C.

Other combinations of techniques may be used. Different transmit and receive event combinations, and/or different combinations of techniques used for transmit and/or receive events (see FIGS. 8B, 10 and 14). Any of the shorting or skipping element techniques may use every element spacing, a greater spacing (e.g. every third element), or more complex groupings (e.g. every two elements or see one receive aperture of FIG. 10). As discussed above, the component apertures used for the synthetic aperture technique may comprise different groups of elements, such as right and left half (see FIG. 8A), every other element (see FIG. 8B), inner and outer groupings (see FIG. 8C), or more complex groupings (see FIG. 10).

Where the number of elements is sufficiently greater than the number of channels being used, the sliding aperture technique may be used in combination with any of the various embodiments discussed above. The transmit and/or receive apertures may be responsive to the sliding aperture technique. A larger effective aperture is provided by combining data responsive to an aperture at different positions. The aperture is slid by one or more elements, and the number of elements may vary, such as sliding one element, then two and then one.

Grating lobes may be minimized. Harmonic imaging may reduce the effect of any grating lobes. Harmonic signals exhibit less side lobe, clutter and grating lobe effects.

Lowering the transmit and receive frequencies as a function of the scan line position reduces the appearance grating lobes. The frequencies are gradually lowered for scan lines spaced away from a center of the scanned region or scan lines closer to an edge of the scanned region. Since the effect of grating lobes increases for larger steering angles, the lower frequencies for larger steering angles counteracts the increased effect. U.S. Pat. No. 5,549,111, the disclosure of which is incorporated herein by reference, discloses this method and associated hardware for implementation.

In one embodiment, the apertures for transmit and receive events vary as a function of the location of the transmit focus. For example, data associated with ranges near a transducer is acquired with small apertures (e.g. apertures defined by a number of elements connected with an equal number of respective channels). As the depth of interest is spaced further from the transducer, the aperture may become larger. To provide a larger aperture with a limited number of channels, the shorting elements, skipping elements, sliding aperture and/or synthetic aperture techniques discussed above are used.

The aperture and associated aperture technique are selected as a function of the transmit focal depth. For example, a plurality of beams are transmitted along each scan line but focused at different depths. For the transmissions focused at deeper depths, the shorting elements, skipping elements, sliding aperture and/or synthetic aperture techniques discussed above are used. Different apertures and associated techniques are used for transmissions focused in the near field. The receive aperture may also be selected as a function of the transmit focal depth. The information associated with the different focal depths along a same scan line is combined to represent the scan line.

In alternative embodiments, only one focal depth is used for each scan line. The aperture technique is set as a function of the focal depth. In yet other alternative embodiments, the transmit and/or receive aperture techniques are varied as a function of parameters associated with the depth of imaging other than the focal depth.

The aperture techniques used may vary as a function of the imaging application, the number of channels and the number of transducer elements. Optimum imaging may be provided by balancing the frame rate with generating of grating lobe effects given the number of channels and transducer elements. Shorting elements, skipping elements, sliding aperture and synthetic aperture techniques may allow optimum imaging given a limited number of transmit or receive channels. Limiting the number of channels allows for more inexpensive manufacture and smaller size of ultrasound systems.

While the invention has been described above by reference to various embodiments, it will be understood that many changes and modifications can be made without departing from the scope of the invention. For example, different multiplexer structures, including layered multiplexers or switching networks with more or fewer switches, may be used to provide for adjacent element shorting or spaced element transmission or reception. Furthermore, imaging based on information received at the fundamental frequency may be used. Different receive and/or transmit configurations using one or both of element shorting or spacing may be used. Shorting or skipping element connections may be provided at the transducer elements, in the handle of the transducer, at the ultrasound system by multiplexers or as part of the designed element spacing (i.e. sparse array).

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A method for obtaining ultrasound data with a medical diagnostic ultrasound system, the method comprising the acts of:

(a) transmitting with a first technique selected from the group consisting of: shorting elements, skipping elements, sliding aperture and combinations thereof; and (b) receiving in response to (a) with a second technique selected from the group consisting of: synthetic aperture, shorting elements, skipping elements, sliding aperture and combinations thereof, where the first technique is different than the second technique.

2. The method of claim 1 wherein (a) comprises transmitting with shorting technique.

3. The method of claim 2 wherein (b) comprises receiving with the synthetic aperture technique.

4. The method of claim 3 wherein (b) comprises receiving with the synthetic aperture technique and the skipping element technique wherein a first receive aperture is associated with odd numbered elements and a second receive aperture is associated with even numbered elements of a transducer array of elements numbered 1–N where N is the total number of elements.

5. The method of claim 2 wherein (a) further comprises transmitting with the sliding aperture technique and (b) comprises receiving with at least the sliding aperture technique.

6. The method of claim 1 wherein (a) comprises transmitting with the skipping element technique.

7. The method of claim 6 wherein (b) comprises receiving with the synthetic aperture technique.

8. The method of claim 7 wherein (b) comprises receiving with the synthetic aperture technique and the skipping element technique wherein a first receive aperture is associated with odd numbered elements and a second receive aperture is associated with even numbered elements of a transducer array of elements numbered 1-N where N is the total number of elements.

9. The method of claim 6 wherein (a) further comprises transmitting with the sliding aperture technique and (b) comprises receiving with at least the sliding aperture technique.

10. The method of claim 1 wherein (a) comprises transmitting with the sliding aperture technique.

11. The method of claim 10 wherein (b) comprises receiving with the shorting element technique.

12. The method of claim 10 wherein (b) comprises receiving with the sliding aperture technique and at least another technique selected from the group consisting of: the synthetic aperture, the shorting, the skipping and combinations thereof.

13. The method of claim 1 further comprising:
(c) changing a transmitted frequency as a function of a scan line position.

14. The method of claim 13 wherein (c) comprises using a lower frequency for scan lines more distant from a center scan line.

15. The method of claim 1 further comprising:
(c) varying transmit and receive techniques as a function of depth of transmit focus.

16. The method of claim 15 wherein (c) comprises varying the transmit and receive techniques as a function of a depth of a transmit focus.

17. The method of claim 1 wherein (a) comprises transmitting with fewer transmit channels than elements in the transducer.

18. The method of claim 1 wherein (b) comprises receiving with fewer receive channels than elements in the transducer.

19. The method of claim 1 wherein (a) comprises transmitting with a sliding aperture and the first technique and (b) comprises receiving with a sliding aperture and the second technique.

20. The method of claim 1 wherein (a) comprises transmitting with the shorting element technique; and further comprising:
(c) implementing the shorting element techniques with a multiplexer having less than 4P switches where a plurality P of transmit channels M and at least 2P transducer elements are provided, the multiplexer operable to connect each transmit channel numbered M to transducer elements numbered M, M+P, M+1 and P+M−1.

21. A method for obtaining ultrasound data with a medical diagnostic ultrasound system, the method comprising the acts of:
(a) transmitting with a first technique selected from the group consisting of: shorting elements, skipping elements and combinations thereof; and
(b) receiving in response to (a) with a second technique selected from the group consisting of: synthetic aperture, shorting elements, skipping elements, and combinations thereof, where the first technique is different than the second technique.

22. The method of claim 21 wherein (b) comprises receiving with the synthetic aperture technique.

23. The method of claim 22 wherein (b) comprises receiving with the shorting elements technique.

24. The method of claim 22 wherein (b) comprises receiving with the skipping elements technique.

25. The method of claim 21 wherein (a) comprises transmittting with the shorting element technique.

26. The method of claim 21 wherein (a) comprises transmitting with the skipping element technique.

27. A method for obtaining ultrasound data with a medical diagnostic ultrasound system, the method comprising the acts of:
(a) transmitting ultrasonic energy;
(b) receiving echo energy in response to (a);
(c) varying an aperture technique of at least one of (a) and (b) as a function of a depth of the transmit focus.

28. The method of claim 27 wherein (c) comprises varying a transmit and a receive aperture technique.

29. The method of claim 27 further comprising wherein (c) comprises varying the receive aperture technique as a function of a depth of transmit focus.

30. The method of claim 27 wherein (a) and (b) comprises transmitting and receiving first and second beams respectively focused to at least two different depths along a same scan line wherein a first aperture technique is used for the first beam and a second aperture technique is used for the second beam.

31. The method of claim 30 wherein (c) comprises connecting a plurality of adjacent elements to an equal plurality of channels for a first depth and using the aperture technique selected from the group of: shorting elements, skipping elements, synthetic aperture and combinations thereof for a second depth deeper than the first depth.

32. The method of claim 30 wherein (c) comprises using the shorting elements technique for the second depth.

33. The method of claim 30 wherein (c) comprises using the skipping elements technique for the second depth.

34. The method of claim 30 wherein (c) comprises using the synthetic aperture for the second depth.

* * * * *